United States Patent
Kim et al.

(10) Patent No.: US 9,841,748 B2
(45) Date of Patent: Dec. 12, 2017

(54) BUILT-IN TYPE VISION BASED INSPECTION TOOL FOR AUTONOMOUS SETTING OF INITIAL ORIGIN

(71) Applicant: KOREA INSTITUTE OF MACHINERY & MATERIALS, Daejeon (KR)

(72) Inventors: Dong-Hoon Kim, Daejeon (KR); Joonyub Song, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 629 days.

(21) Appl. No.: 14/497,871

(22) Filed: Sep. 26, 2014

(65) Prior Publication Data
US 2015/0094844 A1  Apr. 2, 2015

(30) Foreign Application Priority Data
Oct. 2, 2013  (KR) .................. 10-2013-0117848

(51) Int. Cl.
  *G01M 1/38*  (2006.01)
  *G05B 19/401*  (2006.01)
  *G01N 21/88*  (2006.01)

(52) U.S. Cl.
  CPC ....... *G05B 19/401* (2013.01); *G01N 21/8806* (2013.01); *G05B 2219/37555* (2013.01); *G05B 2219/50042* (2013.01)

(58) Field of Classification Search
None
See application file for complete search history.

(56) References Cited

U.S. PATENT DOCUMENTS

| | | | | | |
|---|---|---|---|---|---|
| 4,295,740 | A | * | 10/1981 | Sturges, Jr. ............ | B25J 19/021 244/172.4 |
| 4,316,189 | A | * | 2/1982 | Sturges, Jr. ............ | B25J 19/021 340/870.34 |
| 5,084,827 | A | * | 1/1992 | Demesy ................ | B23Q 17/24 356/243.1 |
| 5,520,569 | A | * | 5/1996 | Endoh .................. | B23B 51/105 408/27 |
| 6,243,019 | B1 | * | 6/2001 | Berns ................... | B23B 13/027 340/686.1 |

(Continued)

FOREIGN PATENT DOCUMENTS

| | | |
|---|---|---|
| EP | 2112461 | 10/2009 |
| EP | 2251120 | 11/2010 |

(Continued)

*Primary Examiner* — Evral E Bodden
(74) *Attorney, Agent, or Firm* — Lex IP Meister, PLLC (57) ABSTRACT

The present invention relates to a vision based inspection tool for setting of an initial origin of an automation machine tool, and more particularly, to a built-in type of vision based inspection tool for setting of an initial origin capable of improving setting precision of a current automation machine tool that depends on initial setting and increasing productivity depending on individual automatic setting by automatically sensing a machining origin in order to perform initial machining and re-machining of an existing workpiece using an automation machine tool and compensating for the machining origin to eliminate a time required for setting machining origins for various shapes in a jog mode.

4 Claims, 4 Drawing Sheets

(56) References Cited

U.S. PATENT DOCUMENTS

| | | | |
|---|---|---|---|
| 7,266,420 B2 * | 9/2007 | Budd | B23Q 17/0909 382/152 |
| 8,082,674 B2 | 12/2011 | Jordil | |
| 2009/0265946 A1 | 10/2009 | Jordil | |
| 2010/0288089 A1 | 11/2010 | Miyamoto | |
| 2013/0278751 A1 * | 10/2013 | Kranitzky | G06T 7/75 348/94 |

FOREIGN PATENT DOCUMENTS

| | | |
|---|---|---|
| JP | H05 228799 | 9/1993 |
| JP | 2010-089182 | 4/2010 |
| KR | 10-2011-0019813 | 3/2011 |
| KR | 10-1072001 | 10/2011 |
| KR | 2011-0107922 | 10/2011 |

* cited by examiner

BUILT-IN TYPE VISION BASED INSPECTION TOOL FOR AUTONOMOUS SETTING OF INITIAL ORIGIN

CROSS-REFERENCE TO RELATED APPLICATION

This application claims priority to and the benefit of Korean Patent Application No. 10-2013-0117848 filed in the Korean Intellectual Property Office on Oct. 2, 2013, the entire contents of which are incorporated herein by reference.

BACKGROUND OF THE INVENTION (a) Field of the Invention

The present invention relates to a vision based inspection tool for autonomous setting of an initial origin of an automation machine tool, and more particularly, to a built-in type of vision based inspection tool for autonomous setting of an initial origin capable of improving setting precision of a current automation machine tool that depends on initial setting and increasing productivity depending on individual automatic setting by automatically sensing a machining origin in order to perform initial machining and re-machine an existing workpiece using an automation machine tool and compensating for the machining origin to eliminate a time required for setting machining origins for various shapes in a jog mode.

(b) Description of the Related Art

When machining is performed using an automation machine tool, a work of manually newly setting a machining origin at the time of performing initial machining and re-machining of an existing workpiece is required, which has a negative influence on machining precision and productivity.

The machining origin indicates a machining start point of a workpiece corresponding to each axis after a machine tool returns to a machine origin in a machining process using the machine tool. The work of setting the machining origin indicates work in which a worker should always contact a workpiece and a tool with each other at a low speed in a jog mode with respect to a new workpiece, and measure and set a relative distance from a machine origin of each axis to the workpiece. Initial position coordinates generated at the time of performing this work has a direct influence on machining precision of the workpiece, and a time delay acts as a representative factor deteriorating productivity. Furthermore, in a current method, friction between the workpiece and the tool is set based on only a visual sense and an auditory sense of the worker, such that there is a limitation in precisely measuring the machining origin, which is a representative factor causing an error in a shape of a product after the machining is performed. Therefore, this manual work should necessarily be eliminated in order to secure productivity and remove the error in the shape of the product.

An attempt to replace the manual work of the machining origin appearing in a machining process of the machine tool with automatic work has been conducted. Conventionally, automatic work of automatically detecting a dimension of a shape of a workpiece by attaching an image sensor to a chuck used in an automatic tool changer (ATC) and obtaining an image of a shape of a machining workpiece at the previous machining origin in real time after the machine tool returns to the machine origin was performed to remove a time delay due to the manual work.

Meanwhile, as existing automatic origin compensation work, a method of automatically setting a machining origin by inputting dimension information of a tool input to the ATC and dimension information of a new workpiece has been representatively used. However, in this method, in the case in which an error is present in the input dimension information of the workpiece and in the case in which an aligning error with each axis occurring when the workpiece is engaged with a vise is present, even though the error is in an allowable range, the machining origin will inevitably have an error.

RELATED ART DOCUMENT

Patent Document

Korean Patent Laid-Open Publication No. 10-2011-0019813

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a built-in type of vision based inspection tool for autonomous setting of an initial origin having advantages of minimizing a time delay due to manual work by sensing recognition of a machining origin generated in a machining process in real time and decreasing an error of a shape by automating recognition of a machining origin based on a visual sense and an auditory sense of a worker.

Particularly, the present invention has been made in an effort to provide a built-in type of vision based inspection tool for autonomous setting of an initial origin having advantages of being widely used in various apparatuses by being configured so as to be built in an apparatus such as an automatic tool changer (ATC).

An exemplary embodiment of the present invention provides a built-in type of vision based inspection tool for autonomous setting of an initial origin provided in a chuck used in an automatic tool changer (ATC) of a machine tool, including:

a docking part provided at one side of the chuck and mounted on the machine tool; an image part provided at one side of the docking part and obtaining an image of a workpiece seated on the machine tool; and an embedded part provided between the docking part and the image part and performing auto-focusing through the image and machining origin setting depending on the auto-focusing.

The image part may include: a camera determining an image size of a machining origin portion of the workpiece and a focal length and irradiating analog type workpiece shape information to a charge coupled device (CCD) cell to digitize the analog type workpiece shape information; a camera fixing part fixing the camera; and an illuminating part providing light to the workpiece.

The embedded part may perform workpiece determining work using an image signal output from the image part and machining origin detecting work in a thickness direction of the workpiece through sharpness of the image and transfer the detected machining origin to a controller of the machine tool, and may transfer the detected machining origin to the controller of the machine tool using RS-232 or Bluetooth wireless communication.

The embedded part may include: a housing coupled to one side of the docking part and having a hollow inner portion; a digital signal processor (DSP) board buried in the other side of the housing; a wireless communication part disposed at one side of the DSP board so as to be spaced apart from the DSP board; and power supply parts disposed between the DSP board and the wireless communication part.

The DSP board and the wireless communication part may be formed in a disk shape in which they have a predetermined diameter based on an axial direction of the chuck, and a plurality of power supply parts may be installed on one surface of the DSP board and be radially disposed based on the axial direction of the chuck.

The DSP board may include: a trigger interface part synchronized with a trigger signal using a machine origin completion signal of the machine tool as the trigger signal to obtain the image; a buffer part storing and processing the previous image in order to prepare for the case of machining the same workpiece as the previous workpiece; a filter part detecting an edge line of the workpiece through the image obtained by the buffer part in order to process the image; an auto-focusing part performing auto-focusing based on sharpness of the image obtained by the trigger interface part so as to detect a machining origin in a thickness direction of the workpiece; and a machining origin detecting part detecting a machining origin using information transferred from the trigger interface part, the buffer part, the filter part, and the auto-focusing part, and the machining origin detected by the machining origin detecting part may be transferred to a controller of the machine tool through the wireless communication part.

The built-in type of vision based inspection tool for autonomous setting of an initial origin according to the present invention having the configuration as described above sets the machining origin generated during the machining of the machine tool through real-time image processing, such that a time delay due to manual setting is decreased, thereby making it possible to increase a production amount per unit time, and such that an error due to the manual setting is eliminated, thereby making it possible to more precisely machine a workpiece.

In addition, in the automatic origin recognizing system and method of the machine tool suggested in the present invention, since information on an existing workpiece may be stored in the embedded apparatus processing the image, the origin may be detected by filtering only a predetermined portion in the obtained image. Therefore, in the case in which work is performed on the same workpiece, a new machining origin may be detected within a very fast time.

Further, since information may be remotely transmitted and received to and from a computer numerical control (CNC) controller and a worker through a Bluetooth based embedded system, which is a wireless communication module, history for the current and previous machining origins may be stored in a database (DB) in real time.

Furthermore, since a vision based inspection tool that is not associated with one machine but may be applied to various machines as a built-in type is generally used in a plurality of machines, a cost due to additional purchase of a vision based inspection tool may be decreased even at the time of replacing a machine.

DETAILED DESCRIPTION OF THE EMBODIMENTS

Hereinafter, an exemplary embodiment of the present invention will be described in detail with reference to the accompanying drawings.

Figure 1:
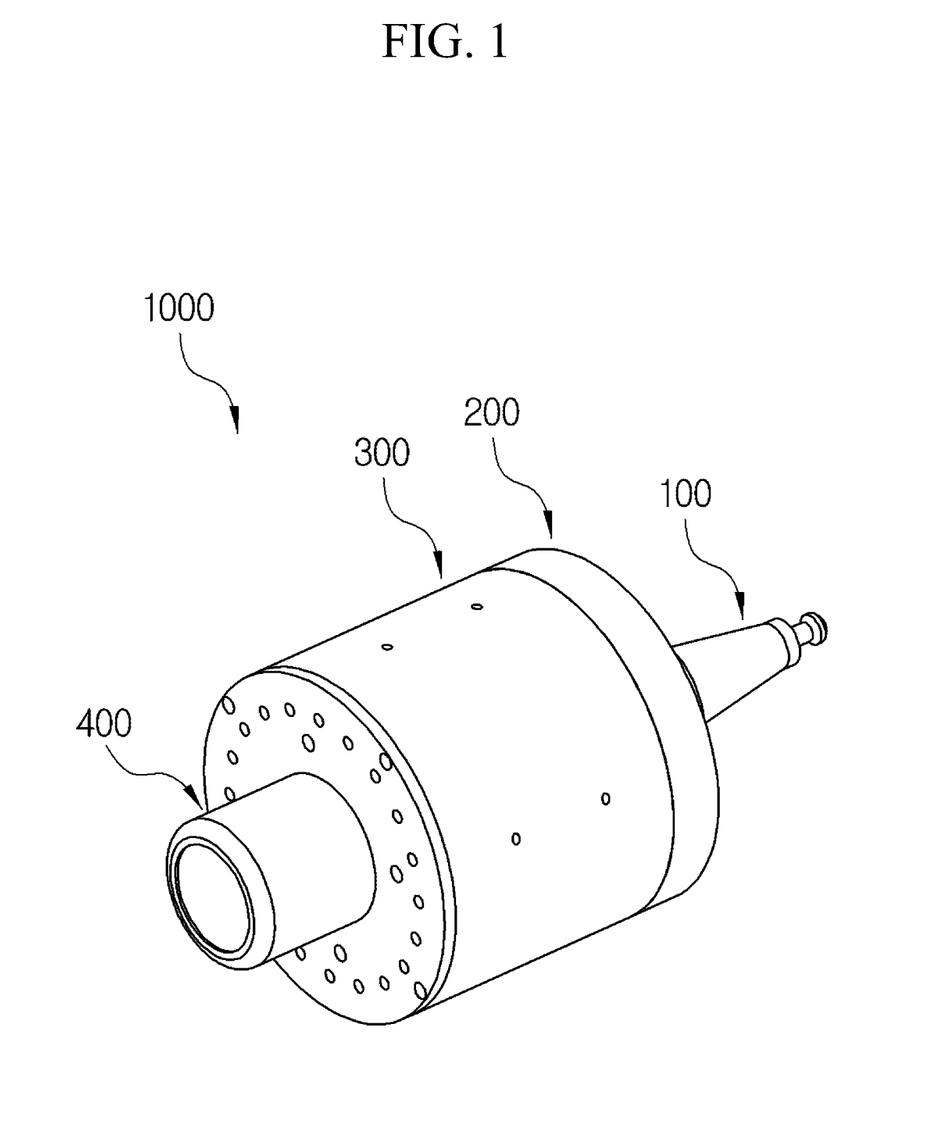
FIG. 1 is an overall perspective view of a vision based inspection tool according to an exemplary embodiment of the present invention.

In FIG. 1, an overall perspective view of a vision based inspection tool 1000 according to an exemplary embodiment of the present invention is shown. As shown in FIG. 1, the vision based inspection tool 1000 is configured to include a chuck 100 provided in a machine tool, a docking part 200 provided at one side of the chuck 100 and mounted on the machine tool, an embedded part 300 provided at one side of the docking part 200 and receiving an image signal of an image part 400 to perform auto-focusing through image processing and machining origin setting depending on the auto-focusing, and the image part 400 provided at one side of the embedded part 300 and obtaining an image of a workpiece seated on the machine tool.

In the vision based inspection tool 1000 having the above-mentioned configuration, the embedded part 300 is not formed separately from the vision based inspection tool 1000 and connected to the machine tool and the image part 400 in a wired scheme, but is provided in the vision based inspection tool 1000 and directly connected to the image part 400 and connected to the machine tool through wireless communication. Therefore, the vision based inspection tool 1000 according to the present invention is configured so as to be attachable to and detachable from the machine tool, such that it may be generally applied to various machine tools that may perform wireless communication.

Hereinafter, a detailed configuration of the vision based inspection tool 1000 according to an exemplary embodiment of the present invention as described above will be described in detail with reference to the accompanying drawings.

Figure 2:
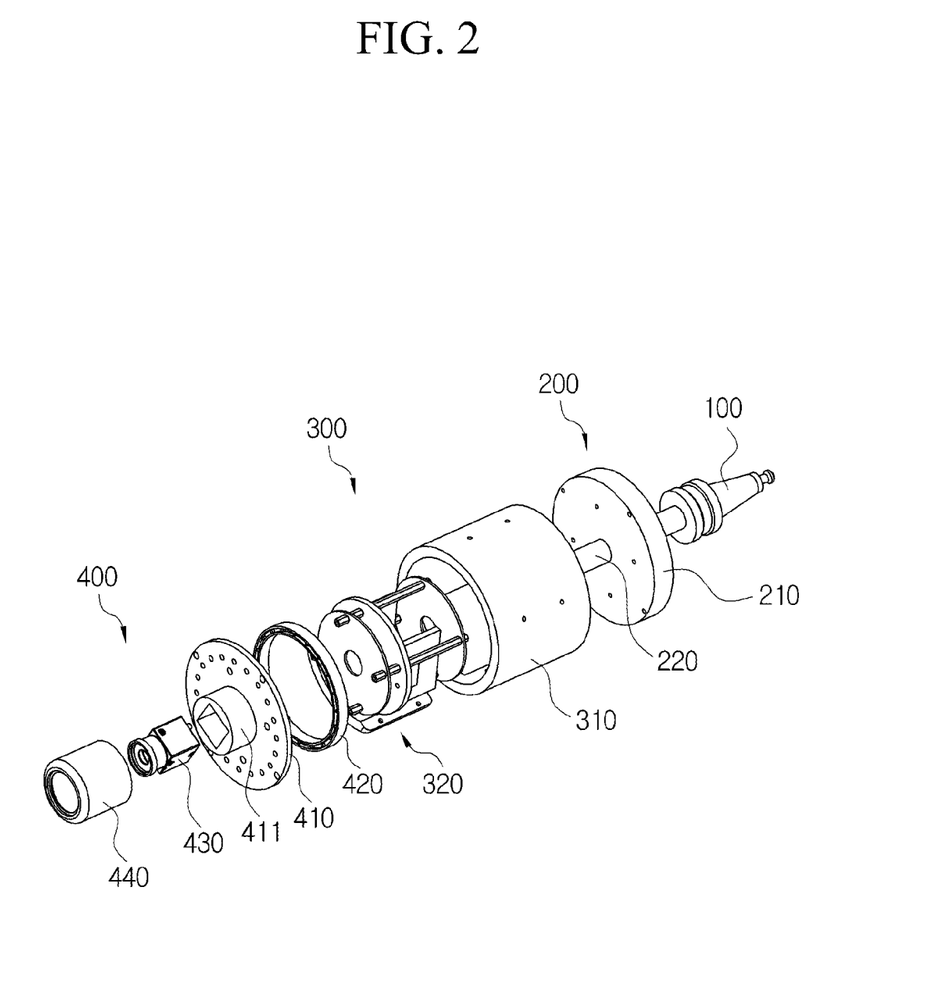
FIG. 2 is an exploded perspective view of the vision based inspection tool according to an exemplary embodiment of the present invention.

In FIG. 2, an exploded perspective view of a vision based inspection tool 1000 according to an exemplary embodiment of the present invention is shown. As shown in FIG. 2, the docking part 200 is provided at one side of the chuck 100, and is configured to include a docking plate 210 having a disk shape and a housing fixing rod 220 having one end fixed to the chuck 100 and having the docking plate 210 and the embedded part 300 fitted into the other end portion thereof.

In addition, the embedded part 300 is disposed at one side of the docking part 200, and is configured to include a housing 310 and an embedded module 320. As shown in FIG. 2, the housing 310 is formed in a cylindrical shape in which one side thereof is opened and the other side thereof is closed, and is configured so as to accommodate the embedded module 320 therein.

The image part 400 is provided at one side of the embedded part 300. The image part 400 is configured to include an illuminating part cover 410, an illuminating part 420, a camera 430, and a camera cover 440.

The illuminating part cover 410 is formed in a disk shape which has a predetermined diameter based on a shaft of the chuck 100, has the illuminating part 420 fixed to one surface thereof, and has a camera fixing part 411 protruding toward one side on the other surface thereof in order to fix the camera 430.

The illuminating part 420 is formed in an annular shape which has a predetermined thickness, and includes a plurality of light emitting diodes (LEDs) radially disposed along an annular circumference so as to provide an amount of light required for obtaining the image.

The camera 430 includes a lens determining an image size of a machining origin portion of the workpiece and a focal length, and irradiates analog-type workpiece shape information input from the lens to a charge coupled device (CCD) cell to digitize the analog type workpiece shape information.

The camera fixing part 411 may be provided with the camera cover 440 in order to prevent damage to the camera 430 due to external impurities at the time of fixing the camera 430 to the camera fixing part 411.

Here, since the embedded part 300 according to the present invention is included in the vision based inspection tool 1000 mounted on the chuck 100 that is rotated, it has the following characteristic configuration in order to minimize an operation error and a communication error, which will be described in detail with reference to the accompanying drawings.

Figure 3:
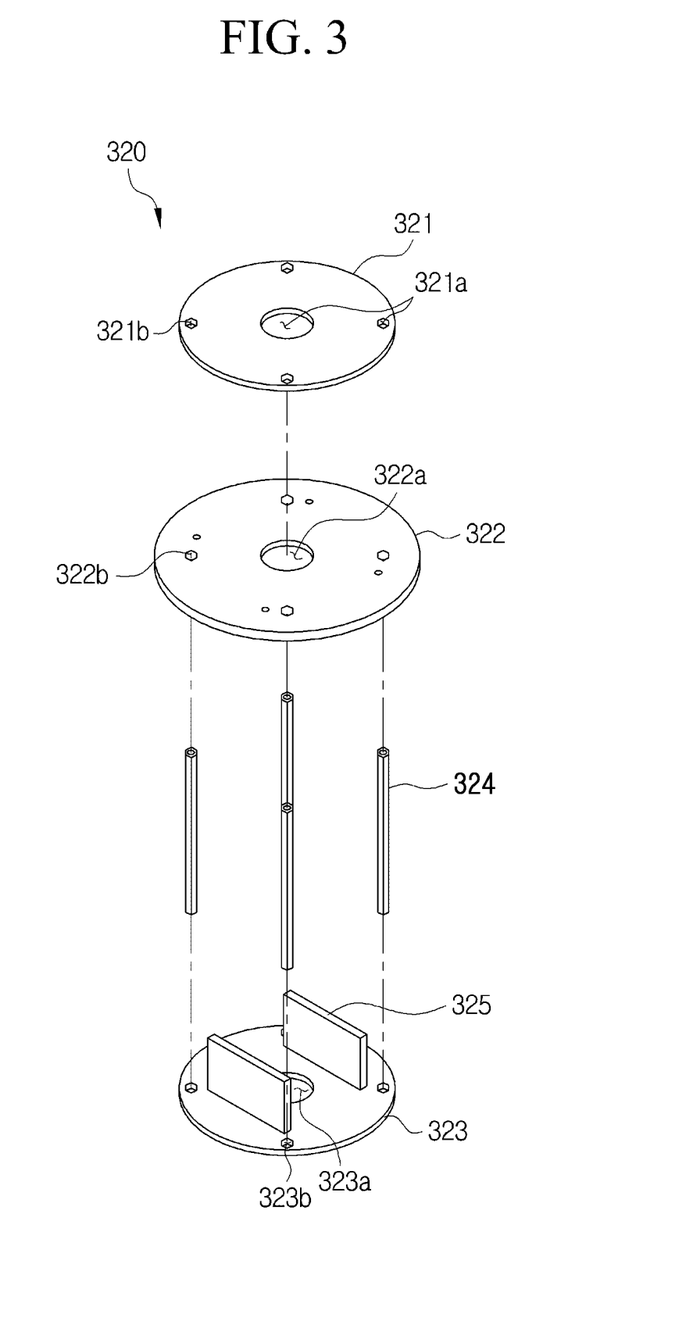
FIG. 3 is a partially exploded perspective view of an embedded part according to an exemplary embodiment of the present invention.

In FIG. 3, an exploded perspective view of the embedded module 320 according to an exemplary embodiment of the present invention is shown. As shown in FIG. 3, the embedded module 320 is configured to include a module cover 321, a wireless communication part 322, a digital signal processor (DSP) board 323, module fixing rods 324, and power supply parts 325.

The module cover 321 is formed in a disk shape so as to close an opened surface of one side of the housing 310 when the embedded module 320 is accommodated in the housing 320, and has a first fixing rod hole 321a formed in the center thereof so that the housing fixing rod 220 penetrates therethrough. In addition, the module cover 321 has a plurality of first fixing parts 321b radially formed at a circumferential part thereof in order to be coupled to the module fixing rods 324.

As the wireless communication part 322, which transfers a signal output from the DSP board 323 to a controller of the machine tool, an RS-232 or Bluetooth wireless communication module may be used. Here, the wireless communication part 322 may be formed in a disk shape which has a predetermined diameter based on the shaft of the chuck 100 in order to minimize a communication error due to rotation of the vision based inspection tool 1000. The wireless communication part 322 has a second fixing rod hole 322a formed in the center thereof so that the housing fixing rod 220 penetrates therethrough. In addition, the wireless communication part 322 has a plurality of second fixing parts 322b radially formed at a circumferential part thereof in order to be coupled to the module fixing rods 324.

The DSP board 323 is a core component of the embedded module 320 for performing workpiece determining work using the image signal output from the image part 400 and machining origin detecting work in a thickness direction of the workpiece through sharpness of the image, and transferring the detected machining origin to the controller of the machine tool. The DSP board 323 is disposed so as to be spaced apart from the wireless communication part 322 in the other side direction by a predetermined distance. Here, the DSP board 323 may be formed in a disk shape which has a predetermined diameter based on the shaft of the chuck 100 in order to minimize an operation error due to the rotation of the vision based inspection tool 1000. The DSP board 323 has a third fixing rod hole 323a formed in the center thereof so that the housing fixing rod 220 penetrates therethrough. In addition, the DSP board 323 has a plurality of third fixing parts 323b radially formed at a circumferential part thereof in order to be coupled to the module fixing rods 324.

The module fixing rods 324, which allow the wireless communication part 322 and the DSP board 323 to be spaced apart from each other by a predetermined distance, are configured so that the wireless communication part 322 and the module cover 321 are fixed to one ends thereof and the DSP board 323 is fixed to the other ends thereof. A plurality of module fixing rods 324 may be radially disposed based on the shaft of the chuck 100.

As the power supply parts 325, which supply power to the wireless communication part 322 and the DSP board 323, general rechargeable batteries may be used. The power supply parts 325 are provided on one side surface of the DSP board 323. Here, the power supply parts 325 have the following characteristic configuration so that the center of gravity of the embedded module 320 does not deviate from the shaft of the chuck 100 at the time of rotation of the vision based inspection tool 1000.

Since the power supply parts 325 have a significant weight, in the case in which they are erroneously disposed, the center of gravity of the embedded module 320 deviates from the shaft of the chuck 100, which causes vibrations at the time of the rotation of the vision based inspection tool 1000. Therefore, a plurality of power supply parts 325 may be radially disposed based on the shaft of the chuck 100.

An operation principle of the DSP board 323 will now be briefly described. The DSP board 323 is configured to include a trigger interface part, a buffer part, a filter part, an auto-focusing part, and a machining origin detecting part.

The trigger interface part is synchronized with a trigger signal using a machine origin completion signal of the machine tool as the trigger signal to obtain the image.

The buffer part stores and processes the previous image in order to prepare for the case of machining the same workpiece as the previous workpiece.

The filter part detects an edge line of the workpiece through the image obtained by the buffer part in order to process the image.

The auto-focusing part performs auto-focusing based on sharpness of the image obtained by the trigger interface part so as to detect a machining origin in the thickness direction of the workpiece.

The machining origin detecting part detects the machining origin using information transferred from the trigger interface part, the buffer part, the filter part, and the auto-focusing part.

The machining origin detected by the machining origin detecting part is transferred to the controller of the machine tool by the wireless communication part 322. Here, the wireless communication part 322 further transfers a minute z axis command commanded by an auto-focusing algorithm performed in the auto-focusing part, together with information on the machining origin, to the controller. Here, the z axis direction indicates the thickness direction of the workpiece.

Figure 4:
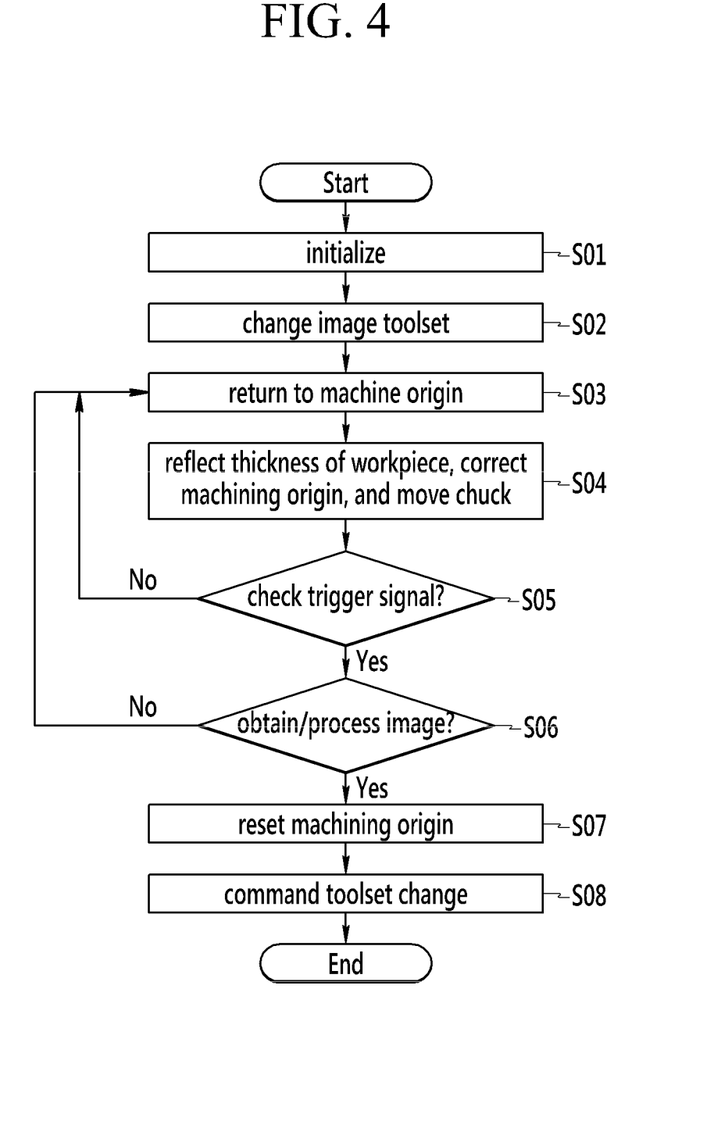
FIG. 4 is a flowchart showing a work sequence of an automatic origin recognizing system and a machine tool.

FIG. 4, which is a flowchart showing a control sequence used at the time of actually applying the vision based inspection tool 1000 as described above, is a flowchart of an automatic machining origin recognizing method of an automatic origin recognizing system of the machine tool as described above.

The automatic machining origin recognizing method of the machine tool includes an initializing step (S01), an image toolset changing step (S02), a machine origin returning step (S03), a machining origin correcting step (504), a trigger signal checking step (S05), an image obtaining/processing step (S06), a machining origin resetting step (S07), and a toolset change commanding step (S08), as shown in FIG. 4. In brief, in a signal processing flow of the automatic origin recognizing system of the machine tool, after a new workpiece is seated in a vise of the machine tool, an automatic tool changer (ATC) mounts the chuck 100 that is remodeled (that is, includes the vision based inspection tool 1000) on a spindle while applying a tool change signal to the machine tool. After the chuck 100 is mounted on the spindle, each axis of the machine tool returns to a machine origin. The embedded part 300 receives a machine origin return completion signal of the machine tool and sets the image part 400 to be in an image obtaining preparation standby state to command the spindle using the wireless communication part 322 to move to a corresponding height of the z axis so as to reflect a thickness of the workpiece and a focal length of the lens that have already been input. The camera 430 obtains an image synchronized with a trigger signal using a command completion signal as the trigger signal, transmits the image to the embedded module 320, and then waits for an image processing completion signal. When the image processing completion signal passes through the embedded module 320, the embedded module 320 transfers a coordinate of the machining origin detected therein to the controller of the machine tool to allow setting of a new machining origin to be completed.

Each step will be described in detail below.

In the initializing step (S01), a) a new workpiece is seated on the machine tool, and a thickness of the workpiece is input to the controller. In the image toolset changing step (S02), b) the chuck 100 including the vision based inspection tool 1000 is mounted in the machine tool. Next, in the machine origin returning step (S03), c) an origin of each axis of the machine tool returns to the machine origin by the controller of the machine tool. Initializing work of substantial machining origin correction is performed by these processes.

Then, in the machining origin correcting step (S04), d) correction of the machining origin in which a thickness of the workpiece is reflected and movement of the chuck 100 are performed by the embedded module 320. After a basic position is determined as described above, in the trigger signal checking step (S05), e) a command for moving the chuck 100 to an initial position in the z axis direction calculated depending on the thickness of the workpiece and the focal length of the lens is performed by the embedded module 320, and work for obtaining the image is performed by the camera 430 using the command as a trigger signal. Here, when the image is not normally obtained (S05-No) in the trigger signal checking step (S05), the automatic machining origin recognizing method returns to the machine origin returning step (S03).

In the image obtaining/processing step (S06), f) sharpness of the image obtained by the embedded module 320 and a machining origin re-collection value depending on the sharpness are calculated when the image is normally obtained (S05—Yes) in the trigger signal checking step (S05).

In the machining origin resetting step (S07), g) the machining origin re-collection value is transmitted to the controller by the embedded module 320 and a position of the chuck 100 is moved by the controller to reset the machining origin, when the machining origin re-collection value is calculated (S06—Yes) in the image obtaining/processing step (S06). Here, when the machining origin re-collection value is not normally calculated in the image obtaining/processing step (S06), the automatic machining origin recognizing method returns to the machine origin returning step (S03).

After the correction of the machining origin is completed through the above-mentioned steps, in the toolset change commanding step (S08), h) a command for changing the chuck 100 with a machining tool chuck is transferred to the machine tool by the controller in order to actually machine the workpiece.

It is not to be interpreted that the spirit of the present invention is limited to an exemplary embodiment described above. The present invention may be applied to various fields and be variously modified by those skilled in the art without departing from the gist of the present invention. Therefore, these modifications and alterations are obvious to those skilled in the art and fall within the scope of the present invention claimed in the claims.

<Description of Symbols>

1000: vision-based inspection tool
100: chuck
200: docking part
210: docking plate
220: housing fixing rod
300: embedding part
310: housing
320: embedded module
321: module cover
322: wireless communication part
323: DSP board
324: module fixing rod
325: power supply part
400: image part
410: illuminating part cover
420: illuminating part
430: camera
440: camera cover

What is claimed is:

1. A built-in type of vision based inspection tool for autonomous setting of an initial origin provided in a chuck used in an automatic tool changer (ATC) of a machine tool, comprising:

a docking part provided at one side of the chuck and mounted on the machine tool;

an image part provided at one side of the docking part and obtaining an image of a workpiece seated on the machine tool; and an embedded part provided between the docking part and the image part and performing auto-focusing through the image and machining origin setting depending on the auto-focusing, and wherein the embedded part includes:

a housing coupled to one side of the docking part and having a hollow inner portion; and an embedded module buried in the hollow inner portion of the housing, and including: a digital signal processor (DSP) board; a wireless communication part disposed at one side of the DSP board so as to be spaced apart from the DSP board; and power supply parts disposed between the DSP board and the wireless communication part, and wherein the DSP board and the wireless communication part are formed in a disk shape in which they have a predetermined diameter based on an axial direction of the chuck, and a plurality of power supply parts are installed on one surface of the DSP board and are radially disposed based on the axial direction of the chuck.

2. The built-in type vision based inspection tool for autonomous setting of an initial origin of claim 1,
wherein the image part includes:
a camera determining an image size of a machining origin portion of the workpiece and a focal length and irradiating analog type workpiece shape information to a charge coupled device (CCD) cell to digitize the analog type workpiece shape information;
a camera fixing part fixing the camera; and
an illuminating part providing light to the workpiece.

3. The built-in type of vision based inspection tool for autonomous setting of an initial origin of claim 2, wherein the embedded part performs workpiece determining work using an image signal output from the image part and machining origin detecting work in a thickness direction of the workpiece through sharpness of the image and transfers the detected machining origin to a controller of the machine tool, and transfers the detected machining origin to the controller of the machine tool using RS-232 or Bluetooth wireless communication.

4. The built-in type vision based inspection tool for autonomous setting of an initial origin of claim 1, wherein the DSP board includes:
a trigger interface part synchronized with a trigger signal using a machine origin completion signal of the machine tool as the trigger signal to obtain the image;
a buffer part storing and processing the previous image in order to prepare for the case of machining the same workpiece as the previous workpiece;
a filter part detecting an edge line of the workpiece through the image obtained by the buffer part in order to process the image;
an auto-focusing part performing auto-focusing based on sharpness of the image obtained by the trigger interface part so as to detect a machining origin in a thickness direction of the workpiece; and
a machining origin detecting part detecting a machining origin using information transferred from the trigger interface part, the buffer part, the filter part, and the auto-focusing part, and
the machining origin detected by the machining origin detecting part is transferred to a controller of the machine tool through the wireless communication part.

* * * * *